United States Patent [19]

Globus

[11] Patent Number: 4,962,208

[45] Date of Patent: Oct. 9, 1990

[54] METHOD FOR PREPARING TIME-STABLE SOLUTIONS OF NON-PYROGENIC MAGNESIUM GLUCONOCITRATES

[76] Inventor: Alfred R. Globus, 26-53 210th St., Bayside, Queens, N.Y. 11360

[21] Appl. No.: 293,990

[22] Filed: Jan. 6, 1989

Related U.S. Application Data

[63] Continuation-in-part of Ser. No. 203,513, May 27, 1988, abandoned, which is a continuation of Ser. No. 65,654, Jun. 24, 1987, abandoned, which is a continuation of Ser. No. 863,428, May 15, 1986, abandoned, which is a continuation-in-part of Ser. No. 778,209, Sep. 20, 1985, abandoned.

[51] Int. Cl.$^5$ ............................................ C07D 313/00
[52] U.S. Cl. ...................................... 549/266; 514/968
[58] Field of Search ...................... 549/292, 222, 266

[56] References Cited

U.S. PATENT DOCUMENTS 3,328,304  6/1967  Globus .................................. 252/80
3,452,049  6/1969  Globus .................................. 549/222

OTHER PUBLICATIONS

Phy. Desk Ref., (PDR), 38th ed., p. 993, (1984).
CRC Handbook of Chem. & Physics, (CRC Handbook), 60th ed., pp. B-68 and B-220, (1979).
U.S. Pharmacopedia-Nat'l Formulary, 15th ed., p. 1044.

*Primary Examiner*—Glennon H. Hollrah
*Assistant Examiner*—Amelia A. Owens
*Attorney, Agent, or Firm*—Evelyn M. Sommer

[57] ABSTRACT

A method is improved for producing highly stable non-pyrogenic solutions of magnesium gluconocitrate. According to this process a specially prepared non-pyrogenic magnesium hydroxycarbonate or magnesium carbonate, gluconic acid anhydride and citric acid are first admixed to form a powder. The admixed powder is then added to an aqueous medium and heated to a temperature of at least about 80° C. to rapidly drive out substantially all of the carbon dioxide. Alternatively, the aqueous medium may be heated to a temperature of at least 80° C. prior to the addition of the powder. The magnesium hydroxycarbonate or magnesium carbonate is prepared by heating to 165° C. for about 18 hours in thin layers in the presence of steam and an oxidizing atmosphere whereby any and all traces of organic material which could be pyrogen forming is eliminated by oxidation thereof.

14 Claims, No Drawings

METHOD FOR PREPARING TIME-STABLE SOLUTIONS OF NON-PYROGENIC MAGNESIUM GLUCONOCITRATES

This application is a continuation-in-part of application Ser. No. 203,513 filed May 27, 1988 which is a continuation of application Ser. No. 065,654 filed June 24, 1987, which in turn is a continuation of application Ser. No. 863,428 filed May 15, 1986 as a continuation-in-part of application Ser. No. 778,209 filed Sept. 20, 1985, all of said prior applications having been abandoned.

FIELD OF THE INVENTION

The present invention relates generally to time-stable non-pyrogenic magnesium gluconocitrate solutions and, more particularly, to a method for producing such non-pyrogenic magnesium gluconocitrate solutions which are extremely stable, microorganism free and which maintain their effectiveness over relatively long periods of time.

DESCRIPTION OF THE PRIOR ART

Solutions of magnesium gluconocitrate are, of course, well known in the art. Such solutions are primarily used for preventing and treating urinary calcifications, which are limited to the lower urinary tract and the bladder. Currently, these solutions are prepared from non-sterile powders which are commercially available under the trademarks Renacidin or Hemiacidrin.

In general, such solutions have been prepared by adding a powdered admixture of magnesium hydroxycarbonate, gluconic acid anhydride and anhydrous citric acid to water wherein they inter-react to form magnesium gluconocitrate. The reaction is accompanied by the release of carbon dioxide which evolves from the liquid. When the evolution of carbon dioxide subsides, the solution is directly poured into heat resistant glass bottles, stoppered and autoclaved.

Unfortunately, however, these and other prior art techniques are not entirely satisfactory from a practical commercial standpoint due to a variety of problems. For example, the art of preparing these solutions which utilizes standard methods has, in the past, produced solutions which have a limited storage life. In addition, a great number of problems have been encountered in the actual preparation of these solutions. For instance, one of the main problems is associated with the continued release of carbon dioxide and the retention of the same in the solution. When the magnesium hydroxycarbonate reacts with the acid components of the mixture, substantial amounts of carbon dioxide are evolved. The carbon dioxide dissolves in the solution and is held therein by the natural solubility of the gas in such solutions. When the solution is thereafter heated in an autoclave, the carbon dioxide gas is evolved in substantially large quantities. As a result, a violent reaction is created within the bottle. In the case where the bottle containing the solution is stoppered, there is a tendency for the bottle to explode. If left unstoppered with the intention of stoppering thereafter, the liquid often overflows the bottle.

This problem is compounded by the fact that after autoclaving, the bottle is permanently sealed. Subsequently, upon storage, the solution begins to cloud and a slight precipitate starts to form. This formation of precipitate increases rather rapidly with time, so that solutions stored for the short period of but several months contain a substantial residue. For these and other reasons, the production of magnesium gluconocitrate from powdered reactants has in the past been limited to medical facilities where autoclaving equipment of sufficient size is available, and where frequency of use enables it to be used before it decomposes.

Further the magnesium hydroxycarbonate as introduced into the admixture is contaminated with microorganisms. These microorganisms, if not eliminated in their entirety, result in the formation of pyrogenic solutions which are totally unacceptable for the intended use.

Utilizing the techniques practiced heretofore, i.e., heating the powdered magnesium hydroxycarbonate prior to use has the effect that the microorganisms in the main are killed. However, those not destroyed and the remains of the destroyed organisms still give rise to the pyrogenic activity of the resultant solutions. The subsequent autoclaving does not eliminate this problem.

Still further, the entirety of the magnesium compounds do not completely enter into solution, the undissolved magnesium compounds exist in the form of microseeds. These microseeds are responsible to a considerable degree for the resultant instability, i.e., the formation of precipitates and clouding of the solution.

Accordingly, there exists a long felt need, which up to now has been unsatisfied, to produce stabilized solutions of magnesium gluconocitrate that are easily produced, and that will retain full activity for many years.

Against the foregoing background, it is a primary object of the present invention to provide a method for producing magnesium gluconocitrate solution's which exhibit stability for long, extended periods of time.

It is another object of the present invention to eliminate the destruction of equipment as well as the rupturing of bottles experienced when the solution is heated in the autoclave.

Yet another object of the invention is to provide a strongly oxidative procedure for producing magnesium hydroxycarbonate whereby any foreign organic matter present will be oxidized and/or gasified.

Still another object of the present invention is to provide a method for producing magnesium gluconocitrate solutions which are non-pyrogenic.

These and other objects will become apparent from the following description of the invention.

SUMMARY OF THE INVENTION

To the accomplishments of the foregoing objects and advantages, the present invention, in brief summary, comprises a method for producing non-pyrogenic magnesium gluconocitrate solution which comprises admixing non-pyrogenic magnesium hydroxycarbonate prepared as hereinafter set forth, gluconic acid anhydride and anhydrous citric acid to form a powder, and thereafter adding the dry powder admixture to an aqueous medium, the mixture of the dried powders in the aqueous medium being heated to a temperature of at least about 80° C. to rapidly and completely remove carbon dioxide from the solution and, thereafter, collecting the magnesium gluconocitrate solution.

In one procedure, the powdered admixture is first added to the aqueous medium which is thereafter rapidly heated to a temperature of at least 80° C.

In another procedure, the aqueous medium is first heated to the required temperature and the powdered admixture is added thereafter.

It is also possible to separately introduce each of the components into a portion of the aqueous medium and then to combine the resulting solutions. The reaction then takes place by heating the combined solutions to a temperature of at least 80 TM C.

Of course, it is, as above noted, possible to have first heated the aqueous medium prior to the introduction of the components: magnesium hydroxycarbonate, gluconic acid anhydride and anhydrous citric acid into the separated aliquots of aqueous medium.

The procedure for the preparation of the magnesium hydroxycarbonate is as hereinafter set forth.

The commercially available starting material, i.e., magnesium hydroxycarbonate is associated with minor but contaminating amounts of organic materials including remains of microorganisms. It is necessary that all of this organic material be eliminated as the same if introduced into the final solutions is likely to act as pyrogenic contaminants.

The starting magnesium hydroxycarbonate material is placed in stainless steel open trays i.e. in the form of thin layers exposed to the air and heated to a temperature of about 165° C. for about 18 hours. During this heating at least 1 molecule of the water of crystallization is driven off as steam. The material exposed to the air and the steam during the heating undergoes oxidation. The presence of moisture (steam) split off in the heating, facilitates the oxidation as the steam keeps the magnesium hydroxycarbonate moving on the tray. The oxidation results in that all traces of organic material including any remains of microorganisms are eliminated.

At the end of about 18 hours the resulting white powder is ground and screened as some lumping may have taken place and introduced into sealed drums for further processing.

While it has been indicated that magnesium hydroxycarbonate is employed as a starting material herein, magnesium carbonate can be used advantageously in place of the magnesium hydroxycarbonated after first having been subjected to an oxidative atmosphere at a temperature of about 165° C. for about 18 hours to render the same non-pyrogenic i.e., free of microorganisms and any other organic material introduced with the magnesium carbonate.

This material is added to the starting mixture of anhydrous citric acid and anhydrous gluconic acid anhydride. During the heating of the solution, which takes place in an unsealed vessel at a temperature of at least 80° C., the reaction between the anhydrous citric acid, gluconic acid anhydride and magnesium hydroxycarbonate takes place to form the magnesium gluconocitrate along with substantial amounts of carbon dioxide being released.

The applicant's prior U.S. Pat. Nos. (3,328,304 and 3,452,049) can be distinguished from that of the application in that the patents teach forming the compositions by mixing the ingredients (all dried prior thereto). The dried mixture is then heated again i.e., "slow and gradual to a temperature above the boiling point of water generally to about 120° C. and most preferably between 110°-25° C. and the heating continued for a period of 15-24 hours . . . " In the patents the heating effects a splitting off of water but "very little carbon dioxide is released during the heating . . . " by adding a powdered admixture of magnesium hydroxycarbonate, gluconic acid anhydride and anhydrous citric acid (which have been previously heated in order to prevent premature reaction during storage) in water wherein they interreact to form magnesium gluconocitrate. The reaction is accompanied by release of carbon dioxide which evolves from the liquid . . . "

The solution is not heated, nor is the water to which the powdered admixture added heated. Admittedly evolution of $CO_2$ occurs in the prior art practice but not of "substantially all thereof", enough being retained to give rise to all of the disadvantages spelled out in the specification.

It is only when the heating of the reaction medium i.e., of the reaction components takes place in the aqueous medium that substantially all of the $CO_2$ is eliminated and a stable solution ensured.

The reaction as herein practiced i.e., the early heating of the solution to at least 80° C. proceeds so that there is no delayed $CO_2$ evolution. This not only avoids explosions in the subsequent autoclave treatment but more importantly avoids the formation of clouding precipitates on storage rendering the solutions unusable.

The invention avoids the delayed $CO_2$ evolution by the early heating of the solution to at least 80° C.

The solution, after the above treatment is filtered (utilizing a conventional micro filter with openings preferably of less than about 10 microns) to remove nuclei which are formed by residual magnesium compounds and carbon dioxide left in the solution.

The solution is acid on reaction having a pH in a 10% solution of 3.9–4.1 and preferably 4.0.

The solution as prepared is non-pyrogenic, contamination by pyrogenic organisms having been eliminated by the heating of the magnesium hydroxycarbonate in a strongly oxidative atmosphere at temperatures of about 165° C. for about 18 hours.

DESCRIPTION OF THE PREFERRED EMBODIMENTS

According to the present invention, the manner of mixing the reactants is not critical. The reactants magnesium hydroxycarbonate (prepared as aforedescribed so that it is non-pyrogenic), gluconic acid anhydride and anhydrous citric acid in a preferred embodiment are previously heated in order to prevent premature reaction during storage. They can be admixed in any convenient manner, such as by introducing them into a suitable vessel. The ratio of reactants can be as follows: magnesium hydroxycarbonate is introduced in an amount from 75–87 grams; the gluconic acid anhydride is introduced in an amount from 21–30 grams; and the anhydrous citric acid is introduced in an amount from 156–171 grams. The reactants are, thereafter introduced into an amount up to 21 grams, and preferably between about 17 to about 21 grams of an aqueous medium and heated to a temperature of at least about 80° C. The aqueous medium can be preheated to the required temperature prior to the introduction of the reactants, or, alternatively, the reactants can be introduced to the aqueous medium which is thereafter rapidly heated to the required temperature. As also disclosed, each of the reactants can be introduced into from about 5–10 grams of the aqueous medium (the total of aqueous medium not exceeding about 21 grams or falling below about 17 grams) and the resulting solutions combined for the reaction.

The aqueous medium is preferably distilled or deionized water. The heating is continued until cessation of carbon dioxide generation. It will be noted that contrary to the prior art, substantially all of the carbon dioxide gas is removed prior to permanent sealing of the containers and subsequent autoclaving.

It has been observed that retention of carbon dioxide in the solution appears to be one of the factors responsible for the formation of nuclei in the solution; thus it is advisable to remove the gas from solution as quickly as possible. However, some nuclei remain which must be removed since the nuclei act as seeds which gradually form considerable precipitation over relatively short periods of time. The nuclei can be conveniently removed by subjecting the solution after treatment as indicated above, to a filtering action. The solution filtered by utilizing a filter with openings preferably less than 10 microns and, most preferably having a pore size of about 8 microns. Said filter is most easily made from sintered metal or from ceramics with carefully selected pore sizes.

Another important aspect of the invention is the pH of the solution which is required to be acid and is preferably about 3.9–4.4, most preferably 4.0.

The solutions are used for dissolution of kidney stones, irrigating indwelling urethral catheters and the urinary bladder in order to dissolve or prevent formation of calcifications. In order to do this, it is clear that an acid solution must be employed i.e., to dissolve a calcification, a neutral or mildly acid solution will not work. It is only with a solution having an acid pH that success for the purpose alleged is obtained. As to irrigating catheters, etc., it is notorious that the material and liquid clinging to the catheter and present in the bladder where such irrigation is indicated is very alkaline. Nothing in the way of cleaning or clearing up the sludgy deposits, etc., would be accomplished other than at the indicated pH.

In addition to the 156–171 grams citric acid, anhydrous) 21–30 grams D-gluconic acid (primarily as the lactone), and 75–87 grams purified magnesium hydroxycarbonate, preferably as inert ingredients, there are, preferably, additionally present 2–6 grams calcium (as the carbonate) and 9–15 grams of magnesium acid citrate ($MgHC_6H_5O_7$). It is this combination separated or together which is introduced into the 17–21 grams of aqueous medium, i.e., distilled water.

The products of the invention find particular use as medicinal agents acting to dissolve calculi of the "staghorn type" having primarily a phosphate composition, especially struvite. The compounds of the invention are particularly useful in dissolving kidney stones and treating alkaline encrusted cystitis, for prophylaxis in the preventing of plugging of catheters by calcium salts and to prevent formation of stones.

The following examples are illustrative of the product and process of the invention, but are not to be construed as limiting.

EXAMPLES

Example 1

164 grams of anhydrous citric acid; 25 grams of gluconic acid anhydride; 80 grams of dried and purified magnesium hydroxycarbonate prepared by heating in a steel tray exposed to the steam and air at 165° C. for 18 hours so that all organic material present has been oxidized; 12 grams of magnesium acid citrate; and 4 grams of calcium as the carbonate were admixed, all in powdered form. Next 20 grams of distilled water was heated to a temperature of 80° C., and then added to the 300 gram heat-resistant glass bottle. The admixed powders were then introduced into the glass bottle containing the heated distilled water and were dissolved therein. The evolvement of carbon dioxide gas from the liquid was observed. When this evolution of carbon dioxide had subsided, the magnesium gluconocitrate solution was filtered, introduced into a glass bottle, stoppered and was placed into the autoclave as is done in the prior art. During autoclaving, the bottle did not break.

Example 2

The same procedure used in Example 1 regarding the admixing of the reactants was followed here. However, this time the distilled water was added to the 300 gram heat-resistant bottle at room temperature. The admixed powder was then dissolved in the water, and the resulting solution was then rapidly heated to a temperature of 80° C. The evolvement of carbon dioxide gas was once again observed. When this had subsided, the bottle was again stoppered, and the solution was autoclaved. The same results were observed here as were observed in Example 1.

Example 3

The procedures followed in Examples 1 and 2 above were independently performed here. However, this time prior to autoclaving the two magnesium gluconocitrate solutions were independently passed through two separate filters which were made of sintered metal, and had pore sizes of 8 microns. Also this time, in both instances, when the powdered admixture was added to the water, and throughout the entire evolutions of the carbon dioxide, the pH of the solution was maintained at a level of 4.0. This solution is now extremely easy to autoclave, and has an almost unlimited stability.

Example 4

The same components and in the amounts as set out in Example 1 were again utilized. In this case, however, the 20 grams of distilled water were split up into three aliquots of 6, 6 and 8 grams. The citric acid was added to 6 grams of the water, the gluconic acid to the second 6 gram aliquot of water and the magnesium hydroxycarbonate, magnesium acid citrate and the calcium carbonate to the 8 gram aliquot of water. The water in each case was at room temperature.

The three solutions were combined in a bottle, heated to a temperature of 85° C. When the evolvement of carbon dioxide was completed, the bottle was sealed and autoclaved.

The solutions produced in accordance with the foregoing examples were not only of unlimited stability but of equal importance, non-pyrogenic.

This solution was particularly well-suited when adjusted to a 10% solution (sterile) in distilled water for irrigating indwelling urethral catheters and the urinary bladder.

The following procedures were carried out for establishing the improved stability of the compositions of the invention as compared to the prior art compositions.

Example 1 of U.S. Pat. No. 3,452,049 was repeated.

A slurry of 3.5 mols of magnesium carbonate and 1 mol of magnesium hydroxide was prepared. The slurried material was dried in order to remove the water and the dried product heated to 115° C. for 16 hours. The resulting powder was ground and added to a mixture of anhydrous citric and gluconic acids. The dried magnesium hydroxycarbonate was employed in an amount of 45 parts by weight, per 100 parts by weight of the dry acid. The mixture was subjected to heating at a temperature of 115° C. for 16 hours. The product was off-white to yellowish in color and had the following composition:

| lactones | percent 59 |
|---|---|
| Magnesium salts of said acids | percent 6 |
| Magnesium hydroxycarbonate | percent 32 |
| Citraconic acid | percent 0.2 |
| Balance | Inert Materials |

The resultant powder was introduced into 20 grams of distilled water to form a solution. The flask was stoppered, autoclaved and stored.

Example 1 of the instant application was repeated i.e., 164 grams of anhydrous citric acid; 25 grams of gluconic acid anhydride; 80 grams of the purified non-pyrogenic magnesium hydroxycarbonate; 12 grams of magnesium acid citrate; and 4 grams of calcium as the carbonate were admixed, all in powdered form. Next 20 grams of distilled water was heated to a temperature of 80° C., and then added to the 300 gram heat-resistant glass bottle. The admixed powders were then introduced into the glass bottle containing the heated distilled water and were dissolved therein. The evolvement of carbon dioxide gas from the liquid was observed. When this subsided, the magnesium gluconocitrate solution was stoppered and was placed into the autoclave.

In the case of the flasks filled with the solutions prepared in accordance with Example 1 of U.S. Pat. No. 3,452,049, upon storage, the solutions began to cloud and a slight precipitate started to form. This formation of precipitate increased rather rapidly with time, so that solutions stored for the short period of but several months contained a substantial residue.

In case of the solutions prepared in accordance with Example 1 of the application, for the period of observation (six (6) months), no precipitation was observed.

The limit of useful life has been established in the applicant's laboratory as well as by the hospitals who have purchased powders as set out in U.S. Pat. No. 3,452,049 and then used the same to prepare 10% solutions, at six (6) months. In both situations, in the applicant's laboratory and in the hospitals, the microcrystals suspended in the solution grow becoming larger and finally settling out of solution. The deposition of the crystals has the untoward results that the composition of the solution is no longer as originally formulated and that the crystals or clumps of them can interfere with the operation of the catheter, as for example by plugging up the openings of the catheter.

This limitation of the useful life of solutions to six months makes it impractical to prepare and store solutions for future use, or to market them.

Of 20 samples prepared as solutions of powders prepared in accordance with U.S. Pat. No. 3,452,049 at the end of six months, 17 had substantial precipitation, 3 were cloudy, and none were satisfactory for further use. When the test was repeated, nine were rejected after three months, eight more were rejected after six months, the other three were on the verge of rejection because of lack of clarity.

By comparison, when the process of the invention was employed to eliminate all carbon dioxide quickly, and to remove the micro-crystals, of twenty bottles of 450 c.c. of solution stored for two years, all were clear, and no change in composition had taken place. At the end of 2½ years, eighteen of the bottles were still clear and free of precipitate (one bottle had accidentally broken, and one stopper had become loose by transfer of the bottles during storage).

In a recent study 1000 bottles of 10% solutions of the product of the invention were prepared, only one was cloudy and it was determined that this was due to a defective stopper.

By using the method and product of the invention, stability is improved so greatly that the product can now be produced, sterilized and stored for almost unlimited periods, can be shipped and distributed as a marketable product with extended shelf life.

Most importantly by using the method and product of the invention, non-pyrogenic magnesium gluconocitrate solutions are prepared which are eminently suitable for their intended purpose, i.e., dissolution of kidney stones, etc.

Having thus described the invention with particular reference to the preferred forms thereof, it will be obvious that various changes and modifications made be made therein without departing from the spirit and scope of the invention as defined by the appended claims.

Wherefore, I claim:

1. A method for producing a timestable non-pyrogenic magnesium gluconocitrate solution which comprises admixing non-pyrogenic magnesium hydroxycarbonate, gluconic acid anhydride and citric acid to form a powder; adding said powdered admixture to an aqueous medium which has been preheated to a temperature of about 80° C. to about 85° C. and is contained in an unsealed vessel, maintaining the resulting mixture at a temperature of about 80° C. to about 85° C. until said ingredients have reacted to form magensium gluconocitrate and carbon dioxide, allowing substantially all of the carbon dioxide to escape from said solution before sealing said vessel, wherein said magnesium hydroxycarbonate has been prepared by drying the magnesium hydroxycarbonate in the form of thin layers in the presence of air and steam at about 165° C. for about 18 hours whereby all traces of organic material are eliminated by oxidation thereof.

2. The method of claim 1, wherein the magnesium gluconocitrate solution is filtered to remove nuclei which are formed by residual carbon dioxide remaining in said solution.

3. The method of claim 2, wherein said solution is filtered using a filter having a pore size no greater than about 10 microns.

4. The method of claim 1, wherein said magnesium gluconocitrate solution has a pH of 4.0.

5. The method of claim 1 wherein said magnesium hydroxycarbonate, gluconic acid anhydride and citric acid are each separately added to an aliquot of said aqueous medium, the aliquots combined and the resultant mixture maintained at a temperature of about 80° C.

6. The non-pyrogenic product produced by the method of claim 1.

7. The method of claim 1 which comprises maintaining the pH of said solution at about 4; filtering said solution to remove nucleii which are formed from residual carbon dioxide from said magnesium gluconocitrate solution, and sealing said vessel.

8. A method for producing a time-stable non-pyrogenic magnesium gluconocitrate solution which comprises admixing non-pyrogenic magnesium hydroxycarbonate, gluconic acid anhydride and citric acid to form a powder; adding said powdered admixture to an aqueous medium contained in an unsealed vessel, heating the resulting mixture to a temperature of about 80° C. to about 85° C., maintaining the resulting mixture at a temperature of about 80° C. to about 85° C. until said ingredients have reacted to form magnesium gluconocitrate and carbon dioxide, allowing substantially all of the carbon dioxide to escape from said solution before sealing said vessel, wherein said magnesium hydroxycarbonate in the form of thin layers in the presence of air and steam at about 165° C. for about 18 hours whereby all traces of organic material are eliminated by oxidation thereof.

9. The method according to claim 8, wherein said filter has a pore size no greater than about 10 microns.

10. The method according to claim 8 wherein said magnesium hydroxycarbonate is replaced by magnesium carbonate.

11. The non-pyrogenic product produced by the method of claim 9.

12. A non-pyrogenic composition for dissolving urinary calcifications consisting essentially of a 10% aqueous solution of the product of claim 8.

13. Method for dissolving urinary calcifications which comprises introducing the composition of claim 12 into the kidney, lower urinary tract and/or bladder for contact with said calcifications.

14. Method for preparing non-pyrogenic magnesium hydroxycarbonate which comprises heating magnesium hydroxycarbonate in the form of thin layers in open steel trays in the presence of air and steam at a temperature of about 165° C. for about 18 hours whereby any organic material present is eliminated by oxidation thereof.

* * * * *